United States Patent
Segal

(10) Patent No.: US 11,559,697 B2
(45) Date of Patent: *Jan. 24, 2023

(54) SYSTEM AND METHOD FOR GENERATING ELECTROMAGNETIC TREATMENT PROTOCOLS FOR THE NERVOUS SYSTEM

(71) Applicant: BrainQ Technologies Ltd., Jerusalem (IL)

(72) Inventor: Yaron Segal, Jerusalem (IL)

(73) Assignee: BRAINQ TECHNOLOGIES LTD., Jerusalem (IL)

( * ) Notice: Subject to any disclaimer, the term of this patent is extended or adjusted under 35 U.S.C. 154(b) by 680 days.

This patent is subject to a terminal disclaimer.

(21) Appl. No.: 16/441,614

(22) Filed: Jun. 14, 2019

(65) Prior Publication Data
US 2019/0358465 A1    Nov. 28, 2019

Related U.S. Application Data

(63) Continuation of application No. 15/257,900, filed on Sep. 6, 2016, now Pat. No. 10,322,295.

(51) Int. Cl.
*A61N 2/02*    (2006.01)
*A61N 2/00*    (2006.01)
(Continued)

(52) U.S. Cl.
CPC .............. *A61N 2/006* (2013.01); *A61B 5/24* (2021.01); *A61B 5/245* (2021.01); *A61B 5/246* (2021.01);
(Continued)

(58) Field of Classification Search
CPC . A61N 2/02; A61N 2/00; A61N 2/004; A61N 2/006; A61B 5/245; A61B 5/246;
(Continued)

(56) References Cited

U.S. PATENT DOCUMENTS 6,463,328 B1   10/2002   John
9,392,956 B2   7/2016    Luo et al.
(Continued)

FOREIGN PATENT DOCUMENTS

CN   1457905    11/2003
CN   1879906    12/2006
(Continued)

OTHER PUBLICATIONS

U.S. Appl. No. 62/642,037, filed Mar. 13, 2018.
(Continued)

*Primary Examiner* — John P Lacyk
(74) *Attorney, Agent, or Firm* — Sughrue Mion, PLLC

(57) ABSTRACT

A system includes a communication interface for receiving information that includes data collected from an array of neural activity sensors that were placed on a patient during a session of applied stimuli. A processor is configured to analyze the received information to obtain a frequency spectrum for each sensor for a given stimulus of the applied stimuli. Neural network frequencies that correspond to an indicated impaired functionality of the nervous system of the patient are selected. For each selected frequencies, a spatial map of neural activity is generated. Each of the generated spatial maps is compared with retrieved corresponding spatial maps to identify treatment frequencies from among the selected neural network frequencies. A treatment protocol is generated for input into an electromagnetic field generator to cause the generator to apply to the patient an electromagnetic field at each identified treatment frequency.

13 Claims, 4 Drawing Sheets

(51) Int. Cl.
  *A61B 5/24*    (2021.01)
  *A61B 5/245*   (2021.01)
  *A61B 5/246*   (2021.01)
  *A61B 5/316*   (2021.01)
  *A61B 5/369*   (2021.01)
  *A61B 5/377*   (2021.01)

(52) U.S. Cl.
  CPC .............. *A61B 5/316* (2021.01); *A61B 5/369* (2021.01); *A61B 5/377* (2021.01); *A61N 2/02* (2013.01)

(58) Field of Classification Search
  CPC ........... A61B 5/369; A61B 5/24; A61B 5/377; A61B 5/316
  See application file for complete search history.

(56) References Cited

U.S. PATENT DOCUMENTS

| | | |
|---|---|---|
| 9,694,197 B2 | 7/2017 | Segal |
| 10,322,295 B2 | 6/2019 | Segal |
| 2004/0002635 A1 | 1/2004 | Hargrove et al. |
| 2006/0122496 A1 | 6/2006 | George et al. |
| 2009/0099627 A1 | 4/2009 | Molnar et al. |
| 2009/0306491 A1 | 12/2009 | Haggers |
| 2010/0016651 A1 | 1/2010 | Sivo |
| 2010/0210894 A1 | 8/2010 | Pascual-leone et al. |
| 2011/0046432 A1 | 2/2011 | Simon et al. |
| 2011/0112427 A1 | 5/2011 | Phillips et al. |
| 2011/0190849 A1 | 8/2011 | Faltys et al. |
| 2011/0295350 A1 | 12/2011 | Mercanzini et al. |
| 2012/0238835 A1 | 9/2012 | Hyde et al. |
| 2012/0271375 A1 | 10/2012 | Wu et al. |
| 2013/0268016 A1 | 10/2013 | Xi et al. |
| 2014/0023999 A1 | 1/2014 | Greder |
| 2014/0148657 A1 | 5/2014 | Hendler et al. |
| 2014/0179986 A1 | 6/2014 | Kelley |
| 2014/0200388 A1 | 7/2014 | Schneider et al. |
| 2014/0303425 A1 | 10/2014 | Pilla et al. |
| 2015/0018706 A1 | 1/2015 | Segal |
| 2015/0105837 A1 | 4/2015 | Aguilar Domingo |
| 2015/0112409 A1 | 4/2015 | Hagedorn |
| 2016/0136427 A1 | 5/2016 | De Ridder |
| 2016/0184599 A1 | 6/2016 | Segal |
| 2016/0213276 A1 | 7/2016 | Gadot et al. |
| 2016/0220836 A1 | 8/2016 | Parks |
| 2018/0064950 A1 | 3/2018 | Segal |
| 2018/0214710 A1 | 8/2018 | Charles et al. |

FOREIGN PATENT DOCUMENTS

| | | |
|---|---|---|
| CN | 104902806 A | 9/2015 |
| EP | 2755550 | 6/2019 |
| WO | 2011/057028 | 5/2011 |
| WO | 2015187712 | 12/2015 |
| WO | 2016/046830 | 3/2016 |
| WO | 2018/047164 | 3/2018 |

OTHER PUBLICATIONS

Xiong, Ye, Asim Mahmood, and Michael Chopp. "Neurorestorative treatments for traumatic brain .injury." Discovery medicine 10.54 (2010): 434.
An International Search Report and a Written Opinion both dated Dec. 20, 2017, which issued during the prosecution of Applicant's PCT/IL2017/050981.
U.S. Appl. No. 62/946,762, filed Dec. 11, 2019.
U.S. Appl. No. 62/946,754, filed Dec. 11, 2019.
An English translation of an Office Action dated Jan. 27, 2016 which issued during the prosecution of Chinese Patent Application No. 201280055647.3.
Niehaus, L., et al. "Abnormal postexcitatory and interhemispheric motor cortex inhibition in .writer's cramp." Journal of neurology 248.1 (2001): 51-52.
Rosenbaum, R. Shayna, et al. "The case of KC: contributions of a memory-impaired person to .memory theory." Neuropsychologia 43.7 (2005): 989-1021.
Emery, Gregory, et al. "Asymmetric Rab11 endosomes regulate delta recycling and specify cell fate .in the *Drosophila* nervous system." Cell 122.5 (2005): 763-773.
Kahana, Michael J. "The cognitive correlates of human brain oscillations." Journal of Neuroscience .26.6 (2006): 1669-1672.
Kernie, Steven G., Trent M. Erwin, and Luis F. Parada. "Brain remodeling due to neuronal and astrocytic proliferation after controlled cortical injury in mice." Journal of neuroscience research .66.3 (2001): 317-326.
U.S. Appl. No. 62/642,038, filed Mar. 13, 2018.
U.S. Appl. No. 61/533,917, filed Sep. 13, 2011.
European Search Report dated Mar. 17, 2015, which issued during the prosecution of Applicant's European App No. 12831890.4.
An International Search Report and a Written Opinion both dated Oct. 22, 2012, which issued during the prosecution of Applicant's PCT/IL2012/000255.
An International Preliminary Report on Patentability dated Mar. 12, 2019, which issued during the prosecution of Applicant's PCT/IL2017/050981.
An English translation of an Office Action dated May 28, 2015 which issued during the prosecution of Chinese Patent Application No. 201280055647.3.
U.S. Appl. No. 62/747,671, filed Oct. 19, 2018.
An English translation of an Office Action dated May 31, 2016, which issued during the prosecution of Japanese Patent Application No. 2014-530377.
An English translation of an Office Action dated Mar. 7, 2017, which issued during the prosecution of Japanese Patent Application No. 2014-530377.
An Office Action dated Jun. 1, 2016, which issued during the prosecution of U.S. Appl. No. 14/344,606.
An Office Action dated Oct. 24, 2016, which issued during the prosecution of U.S. Appl. No. 14/344,606.
An Office Action dated Jun. 29, 2018, which issued during the prosecution of U.S. Appl. No. 15/257,900.
Notice of Allowance dated Apr. 10, 2019, which issued during the prosecution of U.S. Appl. No. 15/257,900.
Notice of Allowance dated Feb. 28, 2019, which issued during the prosecution of U.S. Appl. No. 15/257,900.
Notice of Allowance dated Mar. 20, 2017, which issued during the prosecution of U.S. Appl. No. 14/344,606.
Notice of Allowance dated Apr. 5, 2017, which issued during the prosecution of Australian Patent Application No. 2012310074.
An Office Action dated Apr. 15, 2016, which issued during the prosecution of Australian Patent Application No. 2012310074.
An Office Action dated Mar. 28, 2018, which issued during the prosecution of Canadian Patent Application No. 2,848,549.
An English Translation of an Office Action dated Oct. 19, 2017, which issued during the prosecution of Israel Patent Application No. 231486. (the relevant part only).
An International Search Report and a Written Opinion both dated Mar. 26, 2021, which issued during the prosecution of Applicants PCT/IL2020/051193.
European Search Report dated Dec. 4, 2020 which issued during the prosecution of Applicants European App No. 17848278.2.
European Search Report dated Mar. 13, 2020, which issued during the prosecution of Applicant's European App No. 17848278.2.
An Office Action dated Feb. 17, 2020, which issued during the prosecution of Indian Patent Application No. 2133/DELNP/2014.
Notice of Allowance dated Oct. 21, 2022, which issued during the prosecution of Australian Patent Application No. 2017323663.
An Office Action together with an English Summary dated Aug. 29, 2022 which issued during the prosecution of Korean Patent Application No. 10-2019-7009744.
An Office Action together with an English Summary dated Oct. 17, 2022 which issued during the prosecution of Chinese Patent Application No. 201780068350.3.

SYSTEM AND METHOD FOR GENERATING ELECTROMAGNETIC TREATMENT PROTOCOLS FOR THE NERVOUS SYSTEM

REFERENCE TO RELATED APPLICATIONS

This application is a continuation of U.S. patent application Ser. No. 15/257,900, filed Sep. 6, 2016, entitled "SYSTEM AND METHOD FOR GENERATING ELECTROMAGNETIC TREATMENT PROTOCOLS FOR THE NERVOUS SYSTEM", now U.S. Pat. No. 10,322,295 the disclosure of which is incorporated by reference herein.

FIELD OF THE INVENTION

The present invention relates to treatment of the nervous system. More particularly, the present invention relates to a system and method for generating electromagnetic treatment protocols for the nervous system.

BACKGROUND OF THE INVENTION

Application of time-varying electromagnetic fields has been demonstrated as facilitating restoration of function in the brain and nervous system after trauma, stroke, and spinal cord injury. Application of such therapeutic electromagnetic fields shows potential for future use to treat other conditions of the brain or nervous system, such as autism, Alzheimer's disease, epilepsy, Parkinson's disease, attention deficit hyperactivity disorder (ADHD), or other conditions.

Various techniques have been developed for measuring activity of the brain and nervous system. For example, electroencephalography (EEG) may be utilized to measure overall activity of the brain. Magnetoencephalography (MEG) may be used to map local brain activity near the outer surface of the brain

SUMMARY OF THE INVENTION

There is thus provided, in accordance with an embodiment of the present invention, a system including: a communication interface for receiving information including data collected from an array of neural activity sensors that were placed on a patient during a session of applied stimuli; and a processor configured to analyze the received information to obtain a frequency spectrum for each sensor of the array of sensors for a given stimulus of the applied stimuli; select one or a plurality of neural network frequencies that correspond to an indicated impaired functionality of the nervous system of the patient; for each neural network frequency of the selected one or a plurality of neural network frequencies, generate a spatial map of neural activity for the array of sensors: compare each of the generated spatial maps with one or a plurality of retrieved spatial maps that correspond to that neural network frequency to identify one or a plurality of treatment frequencies from among the one or a plurality of neural network frequencies; and generate a treatment protocol for input into an electromagnetic field generator to cause the generator to apply to the patient to treat the indicated impaired functionality an electromagnetic field at each treatment frequency of the one or a plurality of treatment frequencies.

Furthermore, in accordance with an embodiment of the present invention, the system includes the array of neural activity sensors.

Furthermore, in accordance with an embodiment of the present invention, the array of neural activity sensors includes an array of electroencephalography (EEG) or of magnetoencephalography (MEG) sensors.

Furthermore, in accordance with an embodiment of the present invention, the array of neural activity sensors includes a sensor for measuring neural activity in the spine of the patient.

Furthermore, in accordance with an embodiment of the present invention, the applied stimuli include a stimulus selected from a group of stimuli consisting of an attempt to actively perform a physical or cognitive task, passive movement of a body part, and sensory input.

Furthermore, in accordance with an embodiment of the present invention, the indicated impaired functionality is identified from stored clinical data.

Furthermore, in accordance with an embodiment of the present invention, the generated treatment protocol defines a characteristic of the applied electromagnetic field selected from a group of characteristics consisting of amplitude and duration.

Furthermore, in accordance with an embodiment of the present invention, the generated treatment protocol defines a characteristic of a series of applied electromagnetic fields selected from a group of characteristics consisting of an order of application of electromagnetic fields having different frequencies, an interval between successive applications electromagnetic fields, and a frequency of application of the electromagnetic fields.

Furthermore, in accordance with an embodiment of the present invention, the processor is configured to generate a plurality of different treatment protocols.

Furthermore, in accordance with art embodiment of the present invention, the system includes a treatment system that is configured to apply the therapeutic electromagnetic field in accordance with the generated protocol.

Furthermore, in accordance, with an embodiment of the present invention, the system includes a monitoring sensor for monitoring the patient during application of the therapeutic electromagnetic field.

Furthermore, in accordance with an embodiment of the present invention, the processor is configured to modify an amplitude or duration of the application of the therapeutic electromagnetic field based on the monitoring of the patient.

Furthermore, in accordance with an embodiment of the present invention, the monitoring sensor includes a thermal camera Furthermore, in accordance with an embodiment of the present invention, the monitoring sensor includes a sensor that is configured for placement within the electromagnetic field.

There is further provided, in accordance with an embodiment of the present invention, a system for generating a therapeutic electromagnetic field for treating a patient, the system including: an electrically conductive coil; a generator that is configured to generate an electrical current to flow through the coil in accordance with an input treatment protocol, the treatment protocol generated by a protocol generation system that includes: a communication interface for receiving information including data collected from an array of neural activity sensors that were placed on the patient during a session of applied stimuli: and a processor configured to analyze the received information to obtain a frequency spectrum for each sensor of the array of sensors for a given stimulus of the applied stimuli: select one or a plurality of neural network frequencies that correspond to an indicated impaired functionality of the nervous system of the patient; for each neural network frequency of the selected one or a plurality of neural network frequencies, generate a spatial map of neural activity for the array of sensors: compare each of the generated spatial maps with one or a plurality of retrieved spatial maps that correspond to that neural network frequency to identify one or a plurality of treatment frequencies from among the one or a plurality of neural network frequencies; and generate the treatment protocol to cause the field generator generate the electrical current at each treatment frequency of the one or a plurality of treatment frequencies.

Furthermore, in accordance with an embodiment of the present invention, the generated treatment protocol defines a characteristic of the applied electromagnetic field selected from a group of characteristics consisting of amplitude and duration.

Furthermore, in accordance with an embodiment of the present invention, the system includes a monitoring sensor for monitoring the patient during application of the therapeutic electromagnetic field.

Furthermore, in accordance with an embodiment of the present invention, the processor is configured to modify an amplitude or duration of the application of the therapeutic electromagnetic field based on the monitoring of the patient.

There is further provided, in accordance with an embodiment of the present invention, a method for generating a protocol for application of a therapeutic electromagnetic field to a patient, the method including; receiving via a communication interface information including data collected from an array of neural activity sensors that were placed on a patient during a session of applied stimuli: analyzing the received information to obtain a frequency spectrum for each sensor of the array of sensors for a given stimulus of the applied stimuli; selecting one or a plurality of neural network frequencies that correspond to an indicated impaired functionality of the nervous system of the patient; for each neural network frequency of the selected one or a plurality of neural network frequencies, generating a spatial map of neural activity for the array of sensors; comparing each of the generated spatial maps with one or a plurality of retrieved spatial maps that correspond to that neural network frequency to identify one or a plurality of treatment frequencies from among the one or a plurality of neural network frequencies; and generating a treatment protocol for input into an electromagnetic field generator to cause the generator to apply to the patient to treat the indicated impaired functionality an electromagnetic field at each treatment frequency of the one or a plurality of treatment frequencies.

BRIEF DESCRIPTION OF THE DRAWINGS

In order for the present invention, to be better understood and for its practical applications to be appreciated, the following Figures are provided and referenced hereafter. It should be noted that the Figures are given as examples only and in no way limit the scope of the invention. Like components are denoted by like reference numerals.

DETAILED DESCRIPTION OF THE INVENTION

Figure 1:
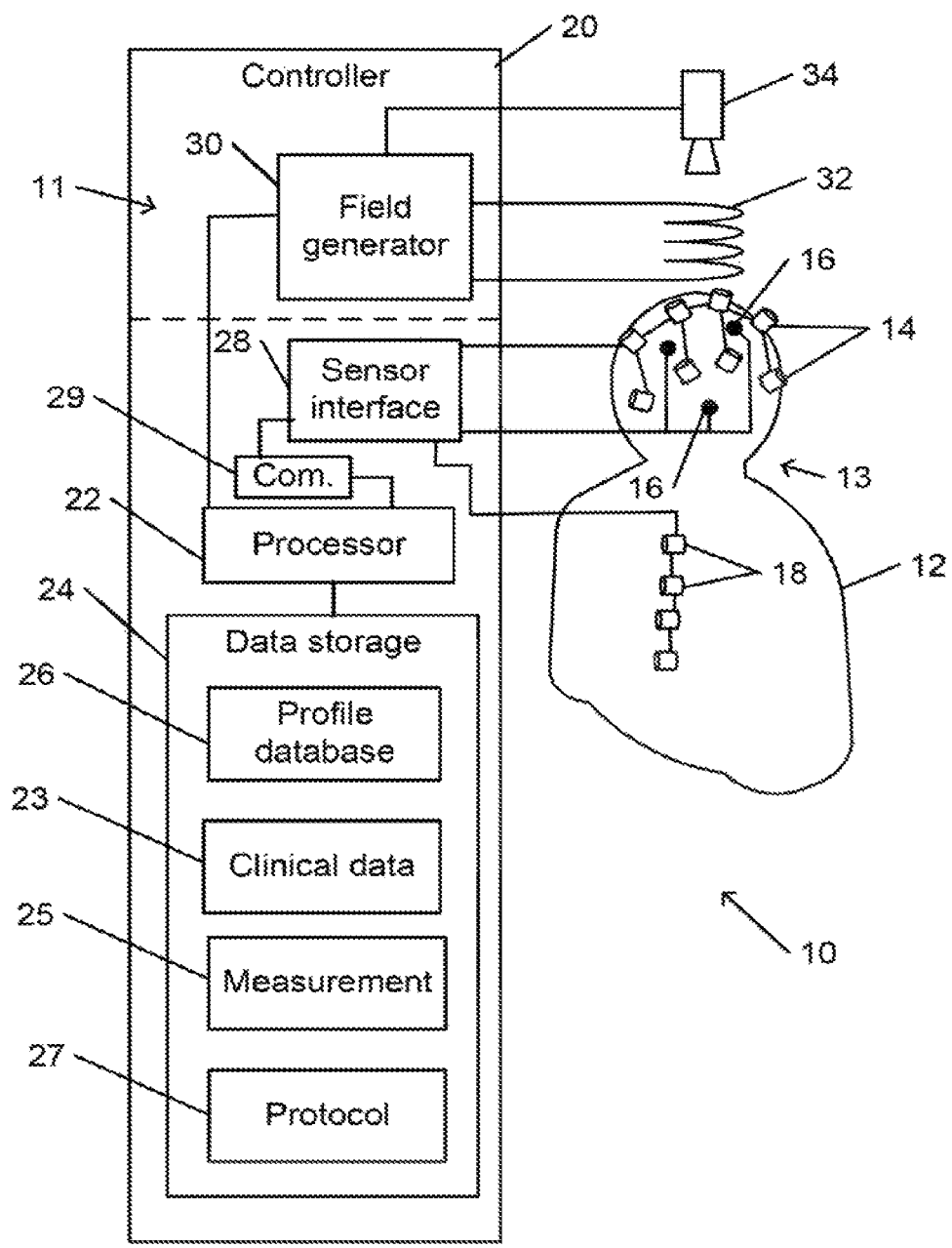
FIG. 1 schematically illustrates a system for generating electromagnetic treatment protocols for the nervous system, in accordance with an embodiment of the present invention.

In the following detailed description, numerous specific details are set forth in order to provide a thorough understanding of the invention. However, it will be understood by those of ordinary skill in the art that the invention may be practiced without these specific details. In other instances, well-known methods, procedures, components, modules, units and/or circuits have not been described in detail so as not to obscure the invention.

Although embodiments of the invention are not limited in this regard, discussions utilizing terms such as, for example, "processing," "computing," "calculating," "determining," "establishing", "analyzing", "checking", or the like, may refer to operation(s) and/or processes) of a computer, a computing platform, a computing system, or other electronic computing device, that manipulates and/or transforms data represented as physical (e.g., electronic) quantities within the computer's registers and/or memories into other data similarly represented as physical quantities within the computer's registers and/or memories or other information non-transitory storage medium (e.g., a memory) that may store instructions to perform operations and/or processes. Although embodiments of the invention are not limited in this regard, the terms "plurality" and "a plurality" as used herein may include, for example, "multiple" or "two or more". The terms "plurality" or "a plurality" may be used throughout the specification to describe two or more components, devices, elements, units, parameters, or the like. Unless explicitly stated, the method embodiments described herein are not constrained to a particular order or sequence. Additionally, some of the described method embodiments or elements thereof can occur or be performed simultaneously, at the same point in time, or concurrently. Unless otherwise indicated, the conjunction "or" as used herein is to be understood as inclusive (any or all of the stated options).

Some embodiments of the invention may include an article such as a computer or processor readable medium, or a computer or processor non-transitory storage medium, such as for example a memory, a disk drive, or a USB flash memory, encoding, including or storing instructions, e.g., computer-executable instructions, which when executed by a processor or controller, carry out methods disclosed herein.

In accordance with an embodiment of the present invention, a protocol for treatment by time-varying magnetic fields is automatically generated by a system. The protocol may be input into a treatment system or device that includes apparatus for generating an oscillating electromagnetic field that may be applied to all or part of the patient. The oscillating electromagnetic field is characterized by a frequency and amplitude or intensity. As used herein the terms "intensity" and "amplitude" are used interchangeably to represent an amplitude, maximum, average, root mean square, or other characteristic or representative value indicative of the strength of an applied electromagnetic field or characterizing a spectrum of a measured neural activity signal (e.g., voltage or current as function of frequency). A treatment protocol may define the frequency and amplitude of the applied field, as well as one or more other characteristics of the field (e.g., duration of each application of the field, number of applications, interval between applications, or other characteristics). A treatment protocol may define two or more fields of different frequencies that may be separately applied to the patient in a defined sequence.

The system may be configured with an interface for receiving information regarding a patient. The information may include clinical data with a description that describes one or more impaired functionalities of the patient. In particular, the description may describe impaired functionality that is known or suspected to be related to impaired function of the patient's nervous system. For example, the clinical data may be input by a medical professional based on examination of the patient, or bused on the patient's statements.

In addition, the received information includes results of measurements of function of the patient's nervous system at various points of the nervous system (e.g., by sensors placed at various locations on the patient's skin, or elsewhere). The measurements may include an array of sensors that are arranged at known locations relative to the patient's brain, spinal cord, or other components of the patient's nervous system. For example, the sensors may include sensors that are designed for electroencephalography (EEG), magnetoencephalography (MEG), or for other types of measurements of neural activity.

Neural activity measurements may be acquired from the patient concurrently with a stimulus session that includes successive application of one or more stimuli. As used herein, a stimulus may be applied actively by the patient. For example, the patient may perform a voluntary physical task (e.g., rest state, moving of a limb or body part, resisting movement of a limb or body part, speaking, controlling breathing, looking at an object, or another active physical task), cognitive (e.g., rest state, imagining a situation, thinking about a particular subject, attempting to solve a problem, concentrating on selected sensory input, or another active cognitive task), attempting to perform a physical task (e.g., concentrating on moving a limb that is paralyzed, has been amputated, or that is restrained), or another voluntary or active task. A stimulus may be applied by an outside agent during which time the patient remains passive. For example, a limb or body part of the patient may be moved by an outside agent (e.g., by another person or by a machine), the patient may be subjected to sensory input, or may otherwise be passively stimulated. Application of a stimulus may include concurrent (or alternating) application of two or more different stimuli. Active or passive application of a stimulus is interchangeably referred to herein as performance of a task.

The neural activity measurement data may be analyzed to obtain a set of frequency spectra (e.g., amplitude of measured activity as a function of signal frequency). For example, each frequency spectrum may represent a measurement by a sensor (or, in some cases, by a group of two or more neighboring or cooperating sensors) during application of a particular stimulus. For example, measurements that were acquired concurrently with application of a particular stimulus may be identified by comparing a time at which the measurements were acquired with a log in which times of application of various stimuli of the session are recorded. Alternatively or in addition, measurements that were acquired during application of a particular stimulus may be marked or labeled with an identification of that stimulus.

One or more frequencies that are relevant to or that are associated with an indicated impaired functionality of the nervous system of the patient may be identified. For example, the impaired functionality may be identified or suspected on the basis of received clinical data (e.g., from symptoms that were reported by the patient or the patient's family or associates, that were noted during examination or observation by a medical professional, or otherwise).

The measured neural activity at each identified frequency may be organized to generate a spatial activity map of the measured neural activity across the nervous system. For example, the spatial position of a measured amplitude may be determined by the identity (e.g., and on a known at least nominal position), of the sensors by which that amplitude was measured. The map may show the amplitude of neural activity at a single identified frequency at each mapped location.

One or more corresponding reference spatial activity maps may be retrieved from a database or other data storage facility. The reference spatial activity maps may be retrieved on the basis of the frequency of the signal whose amplitude is spatially mapped in a corresponding generated spatial activity map. Each reference spatial activity map may show a representative spatial activity for either a healthy nervous system (e.g., based on measurements on subjects whose nervous systems were determined to be functioning without impairment) or for a nervous system whose function is defective in a known manner.

Each of the retrieved reference spatial activity maps may be compared with the corresponding (on the basis of a common signal frequency) generated spatial activity map. Comparison of regions of calculated variations in the activity with respect to the reference spatial activity maps may indicate regions where the generated spatial activity map is indicative of defective function. For example, one or more locations in the comparison between spatial activity maps may indicate a level of function at a spatial region that deviates from a reference spatial activity map that is representative of a healthy nervous system, or a level of function at spatial region that is similar to a reference spatial activity map that is representative of a defectively functioning neural network.

When one or more locations on one or more spatial maps are indicative of defective function at one or more frequencies, a treatment protocol may be generated. The treatment protocol may be input into a device for generating a therapeutic electromagnetic field. The treatment protocol may specify characteristics of one or more time-varying therapeutic electromagnetic fields that are to be applied to the patient. For example, the treatment protocol may specify a subset of the frequencies for which spatial activity maps were generated and at which treatment is indicated. The protocol, when input into the electromagnetic field generator, may cause the electromagnetic field generator to generate a sequence of electromagnetic fields at the specified frequencies. The protocol may specify other characteristics of the sequence of fields. These characteristics may include one or more of field intensities or amplitudes, durations, an order of application of the fields of different frequencies, interval between applications of the different fields, number of applications of each of the fields, or other parameters. The therapeutic field may be applied to the entire body of the patient, or to a part of the body of the patient.

Each identified frequency may be associated with a particular neural network. As used herein, a neural network includes components of the nervous system that are associated with a particular functionality of the nervous system.

Typically, response to a particular stimulus or performance of a particular task may involve two or more different neural networks. For example, movement of a limb in a particular manner may include such functionalities as those related to memory (e.g., remembering the instructions), planning (e.g., the action), activation (e.g., of the limb muscles), control (e.g., of the limb muscles), feedback (e.g., knowing the current position of the limb), or other functionalities.

Relevant Frequencies may have been previously derived from analysis of measurements that were made on a population of subjects. For example, the population may have included both healthy individuals whose nervous system appeared to be fully functional, and individuals whose nervous systems were determined to be functioning defectively in known ways. Detail comparisons among the various measurements may indicate frequencies that are associated which each functionality, and thus with each neural network. Spatial mapping over the nervous system (e.g., of one or more of the brain, spinal cord, or other major nerves) of nervous system activity at a particular frequency may indicate regions of the nervous system where deviation in neural activity is associated with a particular defect in function of a particular neural network.

Reference spatial activity maps may be based on a population of subjects. For example, a reference spatial activity map may be based on an average or other statistical combination of maps that were generated for each member of a population.

Herein, reference may be made to a neural activity profile. A neural activity profile may be based on neural function measurements that are made on a person or a population. The neural activity profile characterizes the neural activity of a person (patient, person in control group, or other person) or population (e.g., after application of averaging or other statistical manipulation to measurements made on individuals in the population). The neural activity profile may be based on EEG, MEG, or other measurements that are made on the brains or other parts of the nervous system of one or more human subjects. For example, sensors similar to MEG sensors, or similar to EEG seniors or other sensors, may be used to measure neural activity in the brain, spinal cord, or in other parts of the nervous system. As used herein, an MEG or EEG measurement refers a measurement any part of the nervous system using an MEG-like or EEG-like sensor, respectively. Similarly, an MEG or EEG sensor, as used herein, refers to a sensor that functions similarly to an MEG (sensing magnetic fields) or EEG (sensing electrical current or voltage) sensor, whether the sensor is intended for measurement of brain activity or activity of another component of the nervous system.

The measurements, in particular EEG, MEG, or similar measurements, may be interpreted to yield a map of measured neural activity at a plurality of identifiable locations in the nervous system. For example, EEG or MEG sensors or other local sensors may be placed at a set of predetermined locations on persons head, back, another location where neural activity occurs (e.g., in the vicinity of an active organ or limb, sense organ, or elsewhere), or at any combination of the above, in order to obtain a spatial map of neural activity. A location of the measured local neural activity may be derived from the location of the sensor or sensor that measured the local activity. In some cases, where the local neural activity is measured by a plurality of sensors, triangulation or other techniques may be applied to determine a location of the measured local activity relative to the known locations of the sensors. In addition, measurements (e.g., functional magnetic resonance imaging (fMRI) or other measurements) may be interpreted to indicate whole brain activity.

The measurements may be made as the nervous system of each subject is activating a particular neural function. For example, a neural function may be associated with the human subject performing one or more tasks. Tasks may include testing (e.g., for the purpose of establishing one or more baseline measurements of neural activity to which other measured neural function may be compared), performing one or more active (e.g., a voluntary movement of a limb, facial feature, or other body part by the patient) or passive (e.g., a part of the body being moved by another person, a machine, or other external agent) motor activities or movements, performing one or more active or passive cognitive tasks (e.g., object recognition, memory retrieval, problem solving, or another cognitive activity), automatic task (e.g., being subjected to an environmental condition, sensory input, or other stimulus that activates the autonomous nervous system), or other tasks. Components of the nervous system where activity is altered from a baseline level during performance of a task are herein referred to as a neural network that is associated with the task and neural function.

A database of representative neural activity profiles may be generated by performing measurements on a population of subjects. The population of subjects may include individuals whose nervous systems are determined to be healthy (e.g., as determined by a lack of known defects in or trauma to their nervous systems). In some cases, the population may be divided into subpopulations (e.g., divided by age, sex, or other characteristics that are known or suspected to affect a neural activity profile). A neural activity profile that is determined for a population that is assumed to be healthy is referred to herein as a reference neural activity profile.

Analysis of the measurement results may yield a pattern of neural activity that is typical for a task or for a family of tasks, e.g., of similar tasks, that are associated with a neural function or activity that is associated with a particular neural network.

Since a measurement by an EEG or MEG sensor typically yields a sensed signal (e.g., typically, in the form of a measured voltage or current corresponding to a sensed electric or magnetic field) as a function of time, the sensed signal may be analyzed to distinguish between frequency components of the signal. For example, the sensed signal may be subjected to an analysis to obtain a spectrum of sensed neural activity. For example, the analysis may include Fourier or other analysis to determine a frequency or wavelength spectrum of the measured signal. Alternatively or in addition, wavelet analysis may be applied to the signal to yield a set of wavelet components. Spectra may be calculated for each sensor measurement result separately, for one or more combinations of sensor measurement results, or a combination of the above. The result is a (hyper-spectral) spatial map of spectral neural activity.

Further analysis of the resulting spectral map may include comparing each obtained spectrum (or set of spectra. e.g., each spectrum corresponding to a particular sensor at a particular location in the brain, spinal cord, or elsewhere in the nervous system) that is associated with one neural function or neural network (e.g., from a signal that is measured during or following performance of a task associated with that neural function or neural network) with spectra that are associated with other neural functions. Such analysis may yield a representative neural activity profile that is characteristic of each neural function of a neural network in a healthy person. A neural activity profile that is characteristic of a function of a particular neural network is herein referred to as a neural network activity profile. Neural network activity profiles from healthy subjects, or a composite neural network activity profile based on a population of healthy subjects, may be stored in a database.

Similar neural activity profiles may be generated for subjects with various known disabilities (e.g., originating from defective function of the nervous system, or due to other causes), or that are known to have various brain-related syndromes. Comparison of these neural activity profiles with the neural activity profiles for healthy subjects may facilitate the process of identifying specific frequencies of specific neural networks where deviations from a healthy neural activity profile are associated with a particular disability or syndrome. For example, such an identified frequency may be indicated by a significant decrease for increase) in amplitude at that frequency that is measured for subjects having a particular known brain disability relative to healthy subjects. In some cases, the measurements that are compared may be made at one or more, locations that known to be associated with a neural network that is related to performance of a particular task. Neural network activity profile of subjects with different disabilities and syndromes, or composite neural network activity profiles based on analysis of a group of individual subjects who are characterized by identical or similar disabilities or syndromes, may also be saved in a database.

In some cases, defective function of a neural network of a patient may be suspected. For example, such defective function may be suspected following stroke, trauma, illness, or another occurrence that may sometimes result in, or that may be suspected of resulting in, injury to one or more components of the nervous system. As another example, the patient may report having difficulty, or may be observed to have difficulty, in successfully performing one or more tasks such that defective functioning of a neural network may be suspected.

When defective functioning of a neural network is suspected, a series of neural activity measurements may be made on the patient. For example, MEG, EEG, or other measurements of neural activity may be made on the patient as the patient performs a series of tasks. The series of tasks may include a complete set of tasks that are used in obtaining a complete neural activity profile of the patient. Alternatively, the performed tasks may be limited to a subset of the tasks that are related to a particular suspected neural network defect or that would be effective in expediting diagnosis of a defect in a particular neural network.

The acquired patient neural activity profile may then be compared with a reference neural activity profile. The reference neural activity profile may include a standard profile for all individuals, or may be characteristic of a subpopulation. For example, the reference neural activity profile may be specific to one or more of a particular age group, gender, racial or ethnic group, professional or academic background, or an otherwise defined subpopulation.

In some cases, the comparison may be limited to those frequencies that are characteristic of or are suspected to be related to a particular suspected defect. For example, the system may be configured to retrieve the frequencies that have been determined to be characteristic of one or more neural networks. The comparison may then check whether measured neural activity differs at one of the identified characteristic frequencies from a reference neural activity profile that is retrieved from a database of reference neural activity profiles.

For example, the comparison may indicate that at one or more locations, the spectrum of neural activity that is associated with a particular neural network as measured for the patient may differ from the reference neural activity profile for that neural network at those locations. The differences may be quantified. For example, a difference score for a neural network may be a function of differences between the measured neural activity profile and the corresponding reference neural activity profile. For example, a difference score may be expressed as a fraction or percent of normal neural activity for each neural network.

The comparison may yield a one or more suggested treatment protocols for an electromagnetic treatment to correct any identified defects in one or more neural networks. For example, the treatment protocol may specify a frequency or frequency spectrum of a therapeutic time varying electromagnetic field that may be applied to the pattern. The treatment protocol may specify a location on the patient to which the specified therapeutic electromagnetic field is to be applied, or may specify that the field is to be applied to the entire brain, to a particular body part, or to the entire body of the patient. The treatment protocol may specify an amplitude of the therapeutic electromagnetic field, or another quantity related to the strength of the therapeutic electromagnetic field that is to be applied. The treatment protocol may specify duration of exposure to the therapeutic electromagnetic field. The treatment protocol may specify a number of treatment sessions, an interval between subsequent treatment sessions, or otherwise define a series of treatments. Where treatment is required for two or more neural networks, a treatment protocol may specify application of treatment (e.g., at two or more field frequencies) for the different neural networks. For example, the protocol may specify an order of treatment (e.g., an order of application of fields having different frequencies or intensities, an interval between successive application of the different fields, or other parameters related to treatment of different neural networks.

In some cases, a protocol may specify a result of a monitored characteristic that may be indicative of the efficacy of the treatment. The treatment may then be modified in accordance with the monitored characteristic. A treatment system, or a treatment monitoring unit of a protocol generation system, may include one or more sensors whose measurements may be indicative of activity in a neural network or in one or more parts of the nervous system. For example, a monitored characteristic may include monitored activity in a region of the brain or the nervous system (e.g., that is associated with a particular activity or neural region) as indicated by the temperature of that region (e.g., where an increase in local temperature is indicative of increased local blood flow, in turn indicative of increased local brain activity). Alternatively or in addition, other sensor may be used. Such other sensors may include, for example, electrocardiogram (ECG) sensors, EEG or MEG sensors, near infrared sensors, blood content analyzers, or another type of sensors. Sensors that are configured for placement on or near the patient, e.g., within the applied therapeutic electromagnetic field, may be configured for operation within magnetic fields (e.g., designed for use during with magnetic resonance imaging (MRI), or on a patient who is located within the magnetic field of an MRI machine). Alternatively or in addition, the treatment system may be configured to apply the therapeutic field intermittently (e.g., with periodic breaks during which no field is applied), with the sensors configured only during breaks between operation of the fields.

For example, an initial protocol may indicate a duration and amplitude of an applied electromagnetic field of a particular frequency that is based on representative results, theory, or otherwise on a typical anticipated response to treatment. However, the response may vary from individual patient to individual patient. Therefore, during application of the treatment field, a temperature map or otter monitoring result of the patients head of nervous system may be acquired, e.g., using a thermal camera or other sensors. For example, a measured temperature may be indicative of whether activity has increased as a result of the treatment in a region of the nervous system that is associated with the neural network that is being treated (e.g., in a part of the brain where activity may be anticipated to increase as a result of the treatment (due to recovery of the neural network in response to stimulation by the applied field).

A treatment system may be configured to adjust or modify a treatment protocol in accordance with one or more monitored quantities. For example, if a monitored temperature has increased to a level that is indicative of improved function of a neural network, treatment with a field frequency that is characteristic of that neural network may be stopped (e.g., for the remainder of a current treatment session, or otherwise) or reduced (e.g., reducing amplitude or duration).

A frequency of a time varying therapeutic field may equal, or may be a function of, a frequency at which the measured neural activity spectrum deviates from the reference neural activity spectrum. Application of the therapeutic time varying field may facilitate regeneration or restoration of capabilities of a neural network.

The difference scores for each neural network may be presented to an operator of the system. A physician or otter healthcare professional may examine the difference scores. In some cases, the protocol generation system may be configured to automatically determine a treatment protocol. In some cases, the protocol generation system may be configured to automatically transmit a treatment protocol to a treatment system. The treatment system may be configured (e.g., when a human operator indicates that treatment is to be applied to the patient for which the treatment protocol was generated) to generate one or more electromagnetic fields in accordance with the transmitted protocol.

The system healthcare professional may then determine whether or not treatment is required, and may prioritize application of one or more of the treatment protocols suggested by the system, for treatment of one or more neural networks. The determination of the treatment protocol by the healthcare professional may be based on. In addition to the initial clinical examination of the patient, patient preference, extent of damage to each neural network, patient history, time limitations, or other information or criteria. Determination of an order of treatment of different neural networks may take into consideration such factors as the patient's needs and preferences, estimated time required to treat each neural network, need for treatment (e.g., as indicated by a difference score in combination with other considerations), past success, or other considerations.

One or more electromagnetic coils may be operated to generate one or more time varying electromagnetic fields in accordance with a selected treatment protocol. The electromagnetic fields may be applied to a selected section of the body (e.g., all or part of the head, torso, thorax, abdominal area, a limb, or another section of the body), or may be applied to the patient's entire body.

FIG. 1 schematically illustrates a system for generating electromagnetic treatment protocols for the nervous system, in accordance with an embodiment of the present invention.

Protocol generation system 10 is configured to generate a treatment protocol for a patient 12. Protocol generation system 10 may be separate from a system that includes treatment system 11 anti that is configured to apply a therapeutic electromagnetic field to patient 12. In some cases, protocol generation system 10 may be configured to communicate with the separate system that includes treatment system 11. In some cases, protocol generation system 10 may be incorporated in a single protocol generation and treatment system that includes treatment system 11 or protocol generation system 10 may incorporate treatment system 11.

Protocol generation system 10 includes, or may communicate with, neural activity sensors 13. Neural activity sensors 13 may include one or more types of sensors that are configured to measure one or more types of neural activity. In some cases, some or all of neural activity sensors 13 for measuring brain activity may be arranged in a helmet, cap, or other headgear or arrangement for placement on or around the head of patient 12. Such an arrangement of neural activity sensors 13 may facilitate reproducible measurements of neural activity at consistent locations. Similarly, neural activity sensors 13 that are configured for measuring neural activity in the spinal cord or elsewhere in the nervous system may be arranged on a shirt, band, sleeve, or other article or garment that may be worn in a consistent manner on the part of patient 12 where neural activity is to be measured.

Neural activity sensors 13 may be incorporated into a stationary unit or a mobile unit. For example, neural activity sensors 13 may be located in a hospital, clinic, rehabilitation center, or within an open environment, or may be portable or transportable to a location of the patient.

For example, neural activity sensors 13 may include an array of MEG sensors 14. Each MEG sensor 14 may be configured to measure a magnetic field that results from electrical currents that are created by neural activity in the brain. Typically, each MEG sensor 14 measures magnetic fields that originate in a region of the brain that is close to that MEG sensor 14. Thus, measurements by an array of MEG sensors 14 may yield a spatial map of neural activity in the brain.

Neural activity sensors 13 may include EEG electrodes 16. EEG electrodes 16 may be configured for attachment to the scalp of patient 12, e.g., at standard locations on the scalp. EEG electrodes 16 may be configured to measure electrical potential at on the scalp. The measured electrical potentials may be indicative of electrical activity within a section of the brain. Thus, measurements by EEG electrodes 16 may yield a measurement of neural activity in the section of the brain near which EEG electrodes are attached.

Neural activity sensors 13 may include spinal neural activity sensors 18. For example, each spinal neural activity sensor 18 may be identical to, or operate similarly to, MEG sensors 14. In this case, an array of spinal neural activity sensors 18 arranged along the spine of patient 12 may measure magnetic fields that result front electrical currents that are created by neural activity in the spinal cord. Thus, measurements using spinal neural activity sensors 18 may yield a map of neural activity within the spinal cord. In some cases, spinal neural activity sensors 18 may be operate similarly to EEG electrodes 16, or in another manner suitable for measuring neural activity in the spinal cord. In some cases, spinal neural activity sensors 18, or other types of sensors, may be configured for placement near, and measurement of, neural activity in other parts of the nervous system (e.g., near one or more nerves).

Neural activity sensors 13 may include other types of sensors for measurement of neural activity.

Controller 20 may include one or more units that are configured to interface with neural activity sensors 13 via sensor interface 28. For example, units of controller 20 may be enclosed in a single case or housing, or may be separate from one another. Separate units of controller 20 may be interconnected by cables, via a wireless connection. In some cases, units of controller 20 may be remote from one another. When units of controller 20 are remote from one another, different units of controller 20 may be configured to communicate with one another via a network or other cable or wireless communication channel. In some cases, part or all of sensor interface 28 may be included in processor 22 (in which case, sensor interface 28 may include only a connection of processor 22 to neural activity sensors 13). In some cases, part or all of the functionality of sensor interface 28 may be provided by processor 22 operating in accordance with programmed instructions.

Sensor interface 28 may include one or more ports or connectors to enable connection of neural activity sensors 13 to controller 20. Sensor interface 28 may include electronics or circuitry that is configured to selectively operate one or more of neural activity sensors 13. Alternatively or in addition, sensor interface 28 may include electronics or circuitry that is configured to selectively receive signals from one or more of neural activity sensors 13. Sensor interface 28 may include electronics or circuitry that are configured to convert a signal that is generated by a neural activity sensor 13 in response to a sensed activity into a signal that is suitable for input to a processor 22 of controller 20. For example, sensor interface 28 may include one or more amplifiers, analog-to-digital converters, filters, or other suitable signal conversion circuitry or electronic components.

In some cases, sensor interface 28 may be external to controller 20. For example, sensor interface 28 may be part of a separate EEG or MEG device. Results of measurements by neural activity sensors 13 may be communicated to controller 20 via communication interface 29.

Communication interface 29 of controller 20 may interface with one or more components that are incorporated into controller 20, or that may communicate with controller 20. For example, communication interface 29 may communicate with an external sensor interface 28. Communication interface 29 may communicate with an input device in order to enable operator input into controller 20. For example, operator input may include clinical data 23, operation commands for controlling operation of a component of protocol generation system 10 for of treatment system 11), or other input data. Communication interface 29 may include a device or port for reading or writing to one or more types of portable or removable data storage media. For example, a data storage medium may be used to store acquired measurement data 25 or clinical data 23 for input into controller 20, or a treatment protocol 27 for input into treatment system 11.

Processor 22 of controller 20 may include one or more processing units, e.g. of one or more computers. For example, processing units of processor 22 may be included in a single case or housing, may include processing units that are housed in separate housings and are interconnected by cables or wirelessly, or may include processing units that are remote from one another and that intercommunicate via a network or other communication channel.

Processor 22 may communicate with data storage device 24. For example, data storage device 24 may include one or more fixed or removable, volatile or nonvolatile memory units or data storage units. Units of storage device 24 may be local (e.g., connected to processor 22 or to one another via a load physical connection) or remote (e.g., accessible to processor 22 via a network or another communication channel, e.g., as in "cloud data storage" or another form of remote data storage unit).

Processor 22 may be configured to operate in accordance with programmed instructions. For example, the programmed instruction may be stored in data storage device 24. Data storage device 24 may be used to store parameters or data to be used by processor 22 when operating in accordance with programmed instructions. Data storage device 24 may be used to store results of operation of processor 22.

Processor 22 may be configured to receive signals from neural activity sensors 13 via sensor interface 28. For example, processor 22 may be configured to control operation of sensor interface 28. A sequence of measurements that are acquired from various neural activity sensors 13 may be determined by programmed instructions stored on data storage device 24. In some cases, an operator of protocol generation system 10 may operate an input device to processor 22 to modify programmed instructions, or to enter special instructions.

Measured quantities may be stored as acquired measurement data 25 on data storage device 24. For example, acquired measurement data 25 may be in the form of a sequence of sensed voltage, current, or other electrical measurements that are acquired at known times. For example, an electrical measurement may be sampled at predetermined successive time intervals (e.g., at equal time intervals or otherwise). Processor 22 may be configured to apply one or more data manipulation techniques to acquired measurement data 23. For example, data manipulation techniques may include applying averaging, digital noise reduction, applying a calibration, scaling, separating a signal form a background signal (e.g., a signal that is acquired when patient 12 is resting or idle), smoothing or sharpening (e.g., applying a low pass or high pass digital filter), or another analysis technique. The result of the data manipulation may be a modified sequence of measured values at successive time intervals and may be stored on data storage device 24 as acquired measurement data 25, either replacing or in addition to acquired measurement data 25 prior to application of data manipulation.

One or more signal processing or other data analysis techniques may be applied to acquired measurement data 25 (e.g., to data as acquired by sensor interface 28 or after application of data manipulation). Application of the data analysis techniques may result in one or more neural network activity profiles. For example, each neural network activity profile result from a data analysis that identifies one or more features that distinguish measured neural activity that is associated with a particular neural network (e.g., based on measurements that are acquired while patient 12 is performing a task that is associated with that particular neural network) from measured neural activity that is associated with a different neural network (or when no neural network is expected to be active, such as when patient 12 is at rest). The resulting neural network activity profiles may be stored as part of profile database 26 on data storage device 24.

For example, acquired measurement data 25 in the form of a time sequence of measured values may be processed to obtain a spectrum in the form of amplitude as a function of frequency. For example, one or more transforms, such as a Fourier transform or wavelet transform, may be applied to acquired measurement data 25. The transform may be applied by utilizing an algorithm such as, for example, the fast Fourier transform (FFT), filtered FFT, wavelet analysis, or another technique. The analysis may be performed separately for each sensor of neural activity sensors 13, for a subset of neural activity sensors 13 (e.g., of the same type at neighboring or functionally linked locations), or for all neural activity sensors 13 (e.g., of a particular type).

Figure 2A:
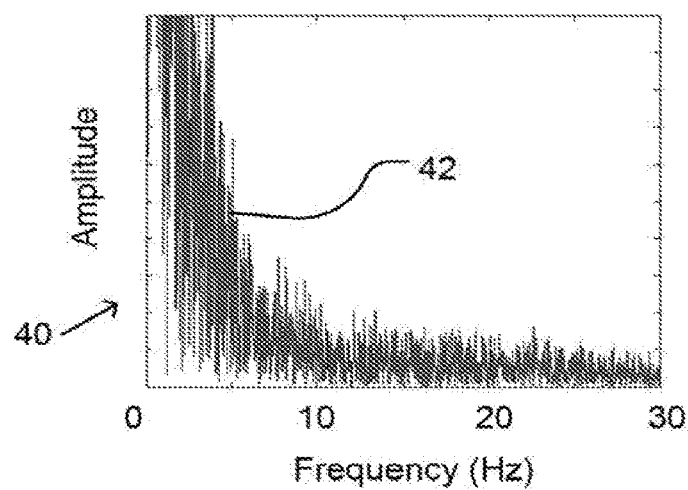
FIG. 2A schematically illustrates a spectrum of signal acquired by a sensor of the system shown in FIG. 1.

FIG. 2A schematically illustrates a spectrum of signal acquired by a sensor of the system shown in FIG. 1.

Signal spectrum 40 graphically illustrates, in the form of spectral neural activity curve 42, a result of spectral analysis of a signal that is acquired by a sensor of neural activity sensors 13 (such as an MEG sensor 14, EEG sensor 16, or spinal neural activity sensor 18).

When data is acquired for group of subjects whose, nervous system is apparently healthy (e.g., the subjects' medical histories are free of any events that may be suspected to injure the nervous system, the subjects are free of any observable symptoms of injury to the nervous system, or are otherwise determined to be healthy), the acquired analyzed data may be combined, e.g., by averaging or by application of another statistical or data combination technique. The resulting combination of each neural network activity profile may be stored in profile database 26 as a reference neural activity profile for a neural network.

A representative neural activity spectrum may result from analysis of neural activity measurements made on a population of apparently healthy subjects during activation of a particular neural network. For example, the neural activity measurement data may have been acquired from neural activity sensors 13 while all of the subjects being measured were performing a single task, or one or more related tasks that are associated with a single neural network. The subjects may have been selected to be representative of a particular population (e.g., age group, gender, common ethnic, racial, professional, educational, or other background, experience, or ability), or to be representative of all apparently healthy human subjects. A representative neural activity spectrum may be part of a set of a plurality of representative neural activity spectra, each representative neural activity spectrum characterizing neural activity at a particular location on the subject's body or nervous system.

Similar measurements and analysts may be performed on subjects whose nervous system is known to function defectively in one or more ways. For example, the defective function may be related to performance of a particular task (e.g., motor, cognitive, sensory, or other task), or may be associated with a known anatomical abnormality (e.g., as determined by an imaging technique, or otherwise). A resulting neural activity spectrum may be compared with a corresponding representative neural activity spectrum. The comparison may yield one or more frequencies that are characteristic of a neural network that is associated with the defective function.

Figure 2B:
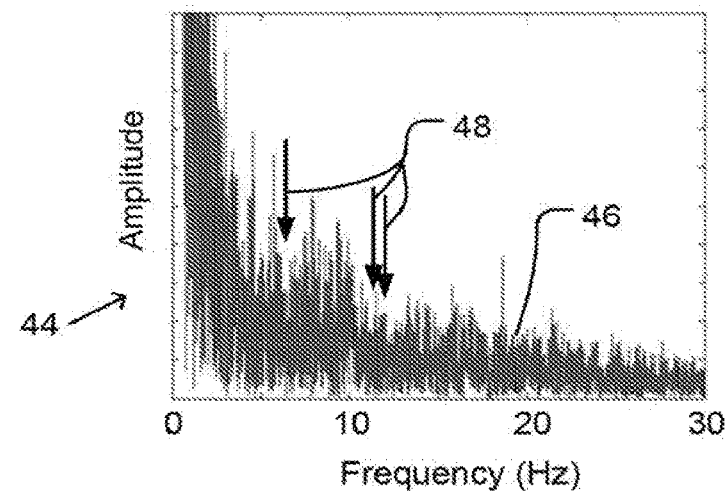
FIG. 2B schematically illustrates identified neural network frequencies in a spectrum such as the spectrum shown in FIG. 2A.

FIG. 2B schematically illustrates identified neural network frequencies in a spectrum such as the spectrum shown in FIG. 2A.

Signal spectrum 44 and spectral neural activity curve 46 may represent a result of spectral analysis of a signal that is acquired by a sensor (or group of sensors) of neural activity sensors 13 on a single subject, or an aggregate result of combination of corresponding measurements on a group or population of subjects. Analysis of comparison of spectra derived from subjects with properly functioning nervous systems and subjects whose nervous systems function defectively in a known manner (e.g., from independent evaluation of the subjects' ability to perform one or more tasks, from identification of an anatomical or physiological abnormality, or otherwise) may identify one or more neural network frequencies 48. For example, defective function of a particular neural network may be associated with a change in amplitude at a particular neural network frequency 48.

One or more of a reference neural network activity profile (a reference neural activity profile that characterizes neural activity of a neural network), identified neural network frequencies 48, representative amplitude (e.g., for healthy subjects) at neural network frequencies 48, or other relevant data may be saved in profile database 26. For example, a set of reference neural activity spectra may be produced during a research or product development phase. For example, a protocol generation system 10 as provided to a user of protocol generation system 10 (e.g., by a manufacturer or other provider) may include a profile database 26 based on neural activity data that was previously acquired during a research or product development phase. Alternatively or in addition, a user of protocol generation system 10 may add or modify a reference neural activity spectrum corresponding to a new or modified reference neural network activity profile.

A user of protocol generation system 10 may measure a neural activity profile on a patient 12 when injury to the patient's nervous system is suspected. Neural activity measurements at one or more locations on the body of patient 12 may be acquired using neural activity sensors 13. Analysis of the measured may result in a patient profile that may be compared with one or more reference neural network activity profiles. In particular, when patient 12 presents symptoms that are associated with defective function of a particular neural network, analysis may be limited to, or may prioritize or emphasize, comparison at neural network frequencies 48 that are associated with that neural network.

The patient neural network activity profile corresponding to a patient neural activity spectrum may be compared by processor 22 to a corresponding reference neural activity spectrum that may be retrieved from profile database 26. For example, the retrieved reference neural activity spectrum may have been calculated using measurements that were acquired under the same or similar circumstances (e.g., at the same or at a similar locution on the body, and during performance of the same task, a similar task or another task that relates directly or indirectly to a suspected deficiency) as were the measurements that were used to calculate a patient neural activity spectrum. For example, reference neural network activity profiles in profile database 26 may be indexed or otherwise arranged to enable retrieval of a reference neural activity spectrum that corresponds to a given patient neural activity spectrum. Such indexing may be in accordance with one or more characteristics of a population or subpopulation, of one or more tasks or neural networks, or other characteristics of a reference neural activity spectrum.

Prior to a patient neural activity spectrum being compared with a retrieved reference neural activity spectrum, one or both of the spectra may be subjected to processing to facilitate the comparison. For example, a normalization technique may be applied to one or both of the spectra in order to enable a comparison between amplitude values at each frequency. Various filtering techniques may be applied to one or both curves to enable selective comparison of coarse or fine features of the spectra. A first or second derivative of the spectra may be calculated in order to enable comparison of slopes, curvatures, or other features of the spectra.

One or more neural network frequencies 48 may be selected for analysts on a spectral neural activity curve 46 that was acquired for a patient. The neural network frequencies 48 may be selected on the basis of clinical data 23. For example, a patient 12 may present one or more symptoms that are recorded in clinical data 23. For example, a symptom may include inability or reduced ability to move a voluntarily limb (e.g., where the skeleton and musculature are intact), to speak, to receive a sensation, to perform a cognitive task (e.g., read, to identify a person or object, to solve a problem, or another cognitive task), or to respond to another type of stimulus. Each symptom could result from impaired function of one or more neural networks (e.g., related to various memory, planning, motor activation, feedback, organization, or other functionality of the nervous system). Each selected neural network frequency 48 may correspond to one of the neural networks. Further analysis then attempt to detect impaired function of one or more of the selected neural networks.

In some cases, a comparison between a patient neural activity spectrum and a corresponding retrieved reference neural activity spectrum may detect one or more differences or deviations between function of a neural network in patient 12 and function of that neural network in a healthy subject. The comparison may identify a frequency or frequency range at which a detected deviation occurs. Such a deviation may be indicative of an anomaly in the behavior of the corresponding neural network.

In particular, the comparison may indicate a deviation in amplitude of the patient neural activity spectrum at one or more neural network frequencies 48. Measured patient neural activity at a particular frequency (e.g., at a neural network frequency 48 or at another frequency) may be spatially mapped over the patient's brain or nervous system.

Figure 2C:
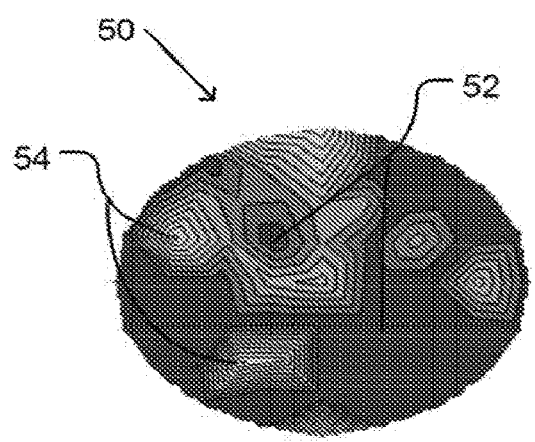
FIG. 2C schematically illustrates a neural activity map for a single frequency.

FIG. 2C schematically illustrates a neural activity map for a single frequency.

Neural activity spatial map 50 represents neural activity at a single frequency (e.g., at an identified neural network frequency 48 or at another frequency) at different parts of the brain (e.g., as measured by corresponding spatially separated sensors of neural activity sensors 13). Neural activity spatial map 50 may represent absolute amplitude at each location, a deviation of a measured amplitude to a retrieved representative amplitude, or another value that represents neural activity at a particular frequency. For example, neural activity spatial map 50 illustrates regions 52 of low activity (e.g., low amplitude), and regions 54 of high activity.

For example, a neural activity spatial map 50 that is generated for patient 12 may be compared with a neural activity spatial map 50 that is retrieved from profile database 26. Processor 22 may be configured to detect differences between the two neural activity spatial maps 50. For example, detection of differences may include subtraction of one of the compared neural activity spatial maps 50 from the other. Further processing may remove artifacts of the subtraction process or otherwise facilitate comparison. For example, processing may remove high spatial frequency features resulting from misalignment, or low spatial frequency features resulting from systematic differences (e.g., due to differences sensor sensitivity, distances front neural activity sensors 13 to components of the nervous system due to differences in body structure, or other systematic differences).

Processor 22 may be configured to generate a treatment protocol 27 based on detected differences between a patient neural activity spectrum and the retrieved reference neural activity spectrum, or between a patient neural activity spatial map 50 and a retrieved neural activity spatial map 50. The generated treatment protocol 27 may be saved on data storage device 24 for retrieval by a user of protocol generation system 10. Alternatively or in addition, the generated treatment protocol 27 may be output for use by an operator of treatment system 11. e.g., via an output device that is in communication with communication interface 29. Alternatively or in addition, e.g., where protocol generation system 10 and treatment system 11 are incorporated into a single system or are configured to intercommunicate, treatment system 11 may automatically retrieve treatment protocol 27 from data storage device 24 when treatment system 11 is to be used to treat the corresponding patient 12.

The generated treatment protocol 27 may be applied by controller 20 in operating field generator 30 configured to generate an electric current to flow through treatment coils 27. Operation of field generator 30 may cause a current to flow through one or more electrically conductive treatment coils 32. The flow of current through treatment coils 32 may generate a therapeutic electromagnetic field that is applied to patient 12. An amplitude of the current flow may determine an amplitude of the therapeutic electromagnetic field. Application of the therapeutic electromagnetic field to patient 12 in accordance with treatment protocol 27 may result in increased neural activity. The increased neural activity may facilitate rehabilitation processes in the nervous system and body of patient 12, and thus facilitate restoration of nervous system function.

One or more monitoring sensors 34 may be used to monitor patient 12 during operation of field generator 30. For example, treatment system 11 may include one or more ports to enable connection of monitoring sensors 34. In some cases, one or more monitoring sensors 34 may be incorporated into one or more components of treatment system 11 (e.g., in a component that includes treatment coils 32, or elsewhere). Monitoring sensors 34 may include one or more sensors, electrodes, or other measurement devices. Measurement devices of monitoring sensors 34 may include one or more thermal cameras, thermocouples or other temperature sensors, multispectral cameras, near infrared sensors. EEG or ECG sensors, active multispectral sensors (e.g., for non-invasive blood chemistry analysis), blood pressure or respiration monitors, eye trackers, invasive (e.g., intravenous) sensors, or other sensors, monitors, or measurement devices. Monitoring sensors 34 may be configured to not interfere with magnetic fields (e.g., may be MRI compatible and manufactured solely out of non ferromagnetic materials) to enable placement in a therapeutic electromagnetic field that is created by treatment coils 32. (In some cases, monitoring measurements may be acquired by monitoring sensors 34 that are placed within the electromagnetic field only during periods where the electromagnetic field is temporarily turned of. In other cases, e.g., where the electromagnetic field is not expected to affect measurements, monitoring may continue during application of the therapeutic electromagnetic field.)

Processor 22 may be configured to permanently or temporarily modify application of protocol 27 (e.g., at least as applied to a specific patient 12) in accordance with one or more quantities that are monitored by monitoring sensors 34. For example, if a value of a monitored quantity deviates from an expected value, processor 22 may be configured to change an amplitude or duration of a therapeutic electromagnetic field that is applied to patient 12 in order to achieve the expected value. As another example, if the value of the monitored quantity is indicative of the treatment being complete (e.g., having had a desired or expected effect on patient 12), continued application of the therapeutic electromagnetic field may be curtailed, reduced, or otherwise modified.

For example, treatment protocol 27 may be generated so as to apply a therapeutic electromagnetic field having a frequency that is approximately equal to the identified frequency where a measured spectrum deviates from a representative spectrum, or having a frequency component at the identified frequency. Alternatively or in addition, the frequency of the applied therapeutic electromagnetic field may be calculated as a function (e.g., harmonic or having another relationship to) the identified frequency. In some cases, an amplitude of the applied therapeutic electromagnetic field at a given frequency may be calculated in accordance with a value of the deviation, or may be based on a predetermined value. In some cases, treatment protocol 27 may indicate a period of time or duration of application of the therapeutic electromagnetic field. The period of time may be for a single treatment session (in which case the protocol may indicate one or more of a frequency of repetition of application of the therapeutic electromagnetic field, a number of times for applying the therapeutic electromagnetic field, and an interval between applications of the therapeutic electromagnetic field). The period of time may include an overall treatment time (e.g., in a situation where different applications of the therapeutic electromagnetic field are expected to have a cumulative effect). Treatment protocol 27 may include a repetition scheme for repeated application of treatments (e.g., for a particular patient or for a class or group of patients).

Alternatively or in addition, a standard treatment protocol 27 may be retrieved from a database of treatment protocols 27. Selection of a particular treatment protocol 27 may be based on a detected deviation of a patient neural activity spectrum from a reference neural activity spectrum.

Figure 3A:
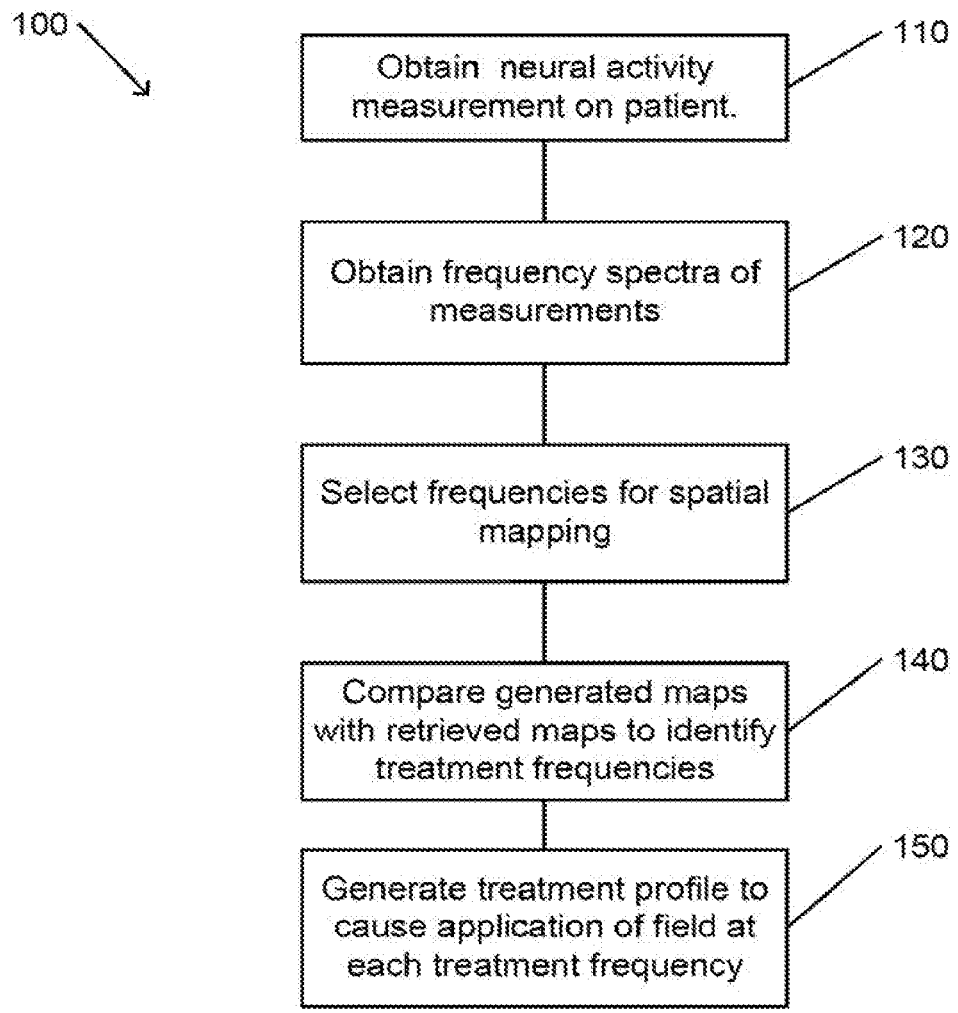
FIG. 3A is a flowchart depicting a method for generating an electromagnetic treatment protocol for treating the nervous system, in accordance with an embodiment of the present invention.

FIG. 3A is a flowchart depicting a method for generating an electromagnetic treatment protocol for treating the nervous system, in accordance with an embodiment of the present invention.

It should be understood with respect to any flowchart referenced herein that the division of the illustrated method into discrete operations represented by blocks of the flowchart has been selected for convenience and clarity only. Alternative division of the illustrated method into discrete operations is possible with equivalent results. Such alternative division of the illustrated method into discrete operations should be understood as representing other embodiments of the illustrated method.

Similarly, it should be understood that, unless indicated otherwise, the illustrated order of execution of the operations represented by blocks of any flowchart referenced herein has been selected for convenience and clarity only. Operations of the illustrated method may be executed in an alternative order, or concurrently, with equivalent results. Such reordering of operations of the illustrated method should be understood as representing other embodiments of the illustrated method.

Treatment protocol generation method 100 may be executed by processor 22 of protocol generation system 10. Treatment protocol generation method 100 may be executed when neural activity sensors 13 are positioned to measure neural activity in patient 12, or after completion of neural activity measurements using neural activity sensors 13.

Results of neural activity measurements using neural activity sensors 13 may be obtained (block 110). For example, acquired measurement data 25 may be retrieved from data storage device 24 or via communication interface 29. Alternatively or in addition, sensor interface 28 may be operated so as to acquire measurements front neural activity sensors 13. The acquired measurement data 25 may include data for different regions of the nervous system, and while patient 12 is performing different tasks or is subjected to a session of different applied stimuli.

In addition to obtaining results of neural activity measurements, clinical data 23 that includes otter relevant information regarding patient 12 may be obtained. For example, clinical data 23 may include a medical history of the patient regarding details of any trauma or illness with regard to patient 12, any symptoms (e.g., physical, behavioral, cognitive, psychological, or other symptoms) that are presented by patient 12, family history, results of other relevant tests, evaluations, or examinations (e.g., MRI, computed tomography, positron emission tomography, or other type of examination), or other relevant information may be obtained. The obtained clinical data 23 may be saved on data storage device 24 as part of acquired measurement data 25, associated with acquired measurement data 25, or otherwise.

The acquired measurement data 25 may be analyzed to calculate a frequency spectrum of one or more measurements of acquired measurement data 25 (block 120). For example, a signal that is detected by each sensor (or by a group of two or more sensors) may be spectrally analyzed to yield a set of spectral neural activity curves 40, e.g., each characterizing neural activity of a neural network at a location as measured by a sensor or by group of sensors (at a single or at neighboring locations, along a single nerve, or otherwise expected to produce a signal that typifies a location within the nervous system). A separate spectral neural activity curve 46 may be calculated for each applied stimulus and for each sensor location.

One or more neural network frequencies 48 may be selected on the basis of clinical data 23, and a neural activity spatial map 50 may be generated for each selected neural network frequency 48 (block 130).

For example, one or more frequencies may be selected on the basis of previously identified correlations between function at that neural network frequency 48 and a symptom or condition that is described by clinical data 23. A separate neural activity spatial map 50 may be generated for each identified neural network frequency 48 and for each stimulus. Each neural activity spatial map 50 may be generated using known spatial coordinates of each neural activity sensor 13. Each point of neural activity spatial map 50 may correspond to one of the spatial coordinates. The value at each point of neural activity spatial map 50 may be determined by the amplitude at the corresponding neural network frequency 48 in the corresponding (as to the location and to the stimulus) spectral neural activity curve 46.

One or more corresponding (e.g., for the same frequency and stimulus) neural activity spatial maps 50 may be retrieved from profile database 26 and compared with the corresponding generated neural activity spatial map 50 for patient 12 (block 140). The various retrieved neural activity spatial maps 50 that correspond to a single generated neural activity spatial map 50 may map neural activity for healthy subjects and for subjects with various known defects in the function of one or more neural networks. The comparison may reveal which neural networks are not functioning properly and are contributing a described condition of patient 12. In this manner, a subset of the identified neural network frequencies 48 may be identified for application of a therapeutic electromagnetic field.

In some cases (e.g., where one or more neural activity sensors 13 are placed at locations that do not exactly conform to locations in a retrieved neural activity spatial map 50). Intercalation, extrapolation, triangulation, or another technique may be applied to enable comparison the same locations.

A treatment protocol 27 may be generated on the basis of the identified subset of neural network frequencies 48 (block 150). The generated treatment protocol 27 may be input into a treatment system 11. Treatment system 11 may then be operated in accordance with treatment protocol 27 to cause field generator 30 to generate an electromagnetic field having a frequency of the identified subset. When the subset includes two or more frequencies, the protocol may cause sequential generation of electromagnetic fields with each frequency of the subset in turn.

The treatment protocol 27 may be generated by selecting a previously designed treatment protocol from a database of previously designed treatment protocols. As another example, a treatment protocol 27 may be generated on the basis of the identified subset, as well as on other factors (e.g., as derived from clinical data 23). For example, an order of application of the different frequencies, or a relative duration of treatment of each neural network, may be determined by an urgency of treatment of each neural network based on seriousness of the deviation from healthy function, on patient requirements or preferences, or on other criteria.

In some cases, more than one treatment protocol 27 may be generated. For example, several different treatment protocols 27 may be generated from which a medical professional may select one for application in treatment.

The generated treatment protocol 27 may be made available for use in operating treatment system 11.

Treatment protocol 27 may specify a sequence of applied electromagnetic field. Each applied electromagnetic field may be characterized by one or more of a frequency, duration, anti amplitude, or by other characteristics. Treatment protocol 27 may indicate an order of application of different electromagnetic fields, frequency of application, interval between successive applications, or other characteristics. Each treatment protocol may be associated with at score or other evaluation that may be considered by a healthcare professional in choosing between two or more suggested treatment protocols 27.

A selected treatment protocol 27 may be applied (e.g., automatically or manually) in operating treatment system 11 to treat patient 12.

Application of treatment protocol 27 may be modified during application of a therapeutic electromagnetic field to patient 12. For example, patient 12 may be monitored during application of the treatment via one or more monitoring sensors 34. Application of the therapeutic electromagnetic field may be modified (e.g., by changing the duration, amplitude, or other characteristic of the applied field) in accordance with a result of the monitoring.

Treatment protocol generation method 100 may be repeated after application of a therapeutic electromagnetic field. For example, treatment protocol generation method 100 may be re-executed when efficacy of treatment is to be evaluated.

Figure 3B:
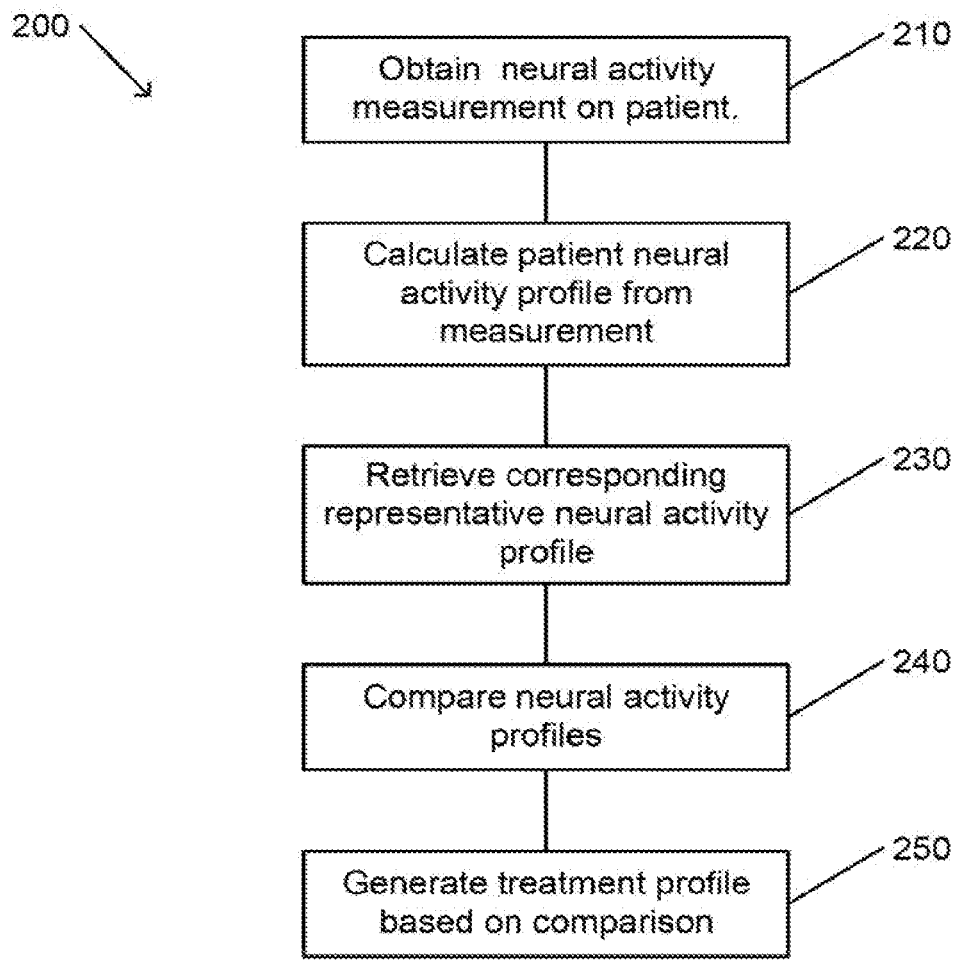
FIG. 3B is a flowchart depicting an alternative method for generating an electromagnetic treatment protocol for treating the nervous system, in accordance with an embodiment of the present invention.

FIG. 3B is a flowchart depicting at) alternative method for generating an electromagnetic treatment protocol for treating the nervous system, in accordance with an embodiment of the present invention.

Treatment protocol generation method 200 may be executed by processor 22 of protocol generation system 10. For example, treatment protocol generation method 200 may be executed (e.g., instead of treatment protocol generation method 200) where computing resources of processor 22 (and data storage resources of data storage device 24) are sufficient to enable comparison of many or all frequencies of neural activity measurements with corresponding retrieved neural activity profiles. Treatment protocol generation method 200 may be executed when neural activity sensors 13 are positioned to measure neural activity in patient 12, or after completion of neural activity measurements using neural activity sensors 13.

Results of neural activity measurements using neural activity sensors 13 may be obtained (block 210). For example, acquired measurement data 25 may be retrieved from data storage device 24. Alternatively or in addition, sensor interface 28 may be operated so as to acquire measurements from neural activity sensors 13. The acquired measurement data 25 may include data for different regions of the nervous system, and while patient 12 is performing different tasks.

In addition to obtaining results of neural activity measurements, other relevant information on the patient may be obtained. For example, a medical history of the patient regarding details of any trauma or illness with regard to patient 12, any symptoms (e.g., physical, behavioral, cognitive, psychological, or other symptoms) that are present by the patient, family history, results of other relevant tests, evaluations, or examinations (e.g., MRI, fMRI, diffusion tensor imaging (DTI), computed tomography, positron emission tomography, or other typo of examination), or other relevant information may be obtained. The obtained information may be saved on data storage device 24 as part of acquired measurement data 25, associated with acquired measurement data 25, or otherwise.

The acquired measurement data 25 may be analyzed to calculate a neural activity profile of patient 12 (block 220). For example, a signal that is detected by each sensor (or by a group of two or more sensors) may be spectrally analyzed to yield a set of spectral neural activity curves 42, e.g., each characterizing neural activity of a neural network at a location or as measured by a sensor or group of sensors. Results of the spectral analysis may be utilized to create one or more neural activity spatial maps 50. For example, separate neural activity spatial maps 50 may be generated for each separate frequency of interest. A frequency of interest may be selected in accordance with a known or suspected condition of patient 12 (e.g., the frequency of interest being associated with a neural network whose function is suspected of being defective based on examination results).

A corresponding reference neural network activity profile that corresponds to the calculated patient neural network activity profile may be retrieved from profile database 26, e.g., as a reference neural activity (block 230). For example, factors considered for selection of a reference neural network activity profile may include one or more of the corresponding neural network, location in the nervous system, and a subpopulation to which patient 12 belongs. One or more neural network frequencies 48 may be selected for retrieval, e.g., on the basis of one or more presented symptoms or other relevant information.

The patient neural network activity profile may be compared with the reference neural network activity profile (block 240). For example, the comparison may be limited to one or more neural network frequencies 48 that are characteristic of one or more neural networks. In some cases, a comparison may be preceded by one or more processing techniques (e.g., normalization or calibration) in order to enable meaningful comparison. For example, a calibration may include adjusting measured values relative to a baseline measurement (e.g., acquired when the patient is at rest, or otherwise in the absence of strong stimuli).

In some cases (e.g., where one or more neural activity sensors 13 are placed at locations that do not exactly conform to locations in a retrieved reference neural network activity profile), interpolation, extrapolation, triangulation, or another technique may be applied to enable comparison at a single location.

A treatment protocol 27 may be generated on the basis of the comparison (block 250). For example, the comparison may reveal one or more significant deviations of the patient neural network activity profile from a corresponding reference neural network activity profile. A deviation (e.g., calculated as an arithmetic difference in amplitude at one or more frequencies, or otherwise) may be considered to be significant if it exceeds a threshold value, if it correlates with a difference at another related frequency or at another related location, if it correlates with supplementary information (e.g., patient symptoms or other information), or in accordance with other criteria.

The treatment protocol 27 may be generated by selecting a previously designed treatment protocol from a database of previously designed treatment protocols. The selection of a particular treatment protocol may be based on a similarity between a detected deviation and a characteristic deviation that is associated with the selected treatment protocol 27. As another example, a treatment protocol 27 may be generated on the basis of the detected deviation in accordance with one or more protocol generation algorithms (e.g., on the basis of a characteristic frequency or magnitude of the detected deviation).

A treatment protocol 27 may include treatment that is directed to a single neural network, or to two or more neural networks. When directed to a plurality of neural networks, treatment protocol 27 may specify an order of the different treatments (e.g., applying fields of different frequencies) that are directed to the different neural networks.

In some cases, more than one treatment protocol 27 may be generated. For example, where execution of treatment protocol generation method 200 is repeated for different neural networks or for different locations, one or more different treatment protocols 27 may be generated. In this case, each generated treatment protocol 27 may be accompanied by a score that indicates a degree of need or urgency for application of each treatment protocol 27, or an indication of an expected success (e.g., based on past experience). An operator of treatment system 11 (e.g., a healthcare professional) may apply the treatment protocols in an order determined by the scores, or may modify the order. For example, a treatment protocol 27 may be accepted, rejected, or modified based on clinical data or judgment, time constraints, availability of treatment facilities, prognosis, with regard to different neural networks, patient needs or preferences, or on the basis of other criteria. For example, due to specific (e.g., professional, familial, or personal) needs of a particular patient 12, it may be determined that treatment of one neural network is more urgent than treatment of another.

The generated treatment protocol 27 may be made available for use in operating treatment system 11.

Treatment protocol 27 may specify one or more treatment sessions. Each treatment session may be characterized by one or more of a frequency, duration, amplitude of the applied electromagnetic field, or by other characteristics. Treatment protocol 27 may indicate a scheme for applying one or more specified different treatment sessions. The scheme may be characterized by an order of application of the different treatment sessions, frequency of application, interval between applications, or other characteristics. Each treatment protocol may be associated with at score or other evaluation that may be considered by a healthcare professional in choosing between two or more suggested treatment protocols 27.

A selected treatment protocol 27 may be applied (e.g., automatically or manually) in operating treatment system 11 to treat patient 12.

Application of treatment protocol 27 may be modified during application of a therapeutic electromagnetic field to patient 12. For example, patient 12 may be monitored during application of the treatment via one or more monitoring sensors 34. Application of the therapeutic electromagnetic field may be modified (e.g., by changing the duration, amplitude, or other characteristic of the applied field) in accordance with a result of the monitoring. For example, when treatment protocol 27 defines a session in which therapeutic electromagnetic fields of different frequencies are sequentially applied, monitoring may indicate that application of one of the fields has been adequate. In this case, application of that field may be halted (e.g., resetting the duration to the elapsed period of application of the field, resetting the amplitude to zero, or both) so as to cause the next field (of different frequency) of the defined session to be applied.

Treatment protocol generation method 200 may be repeated after application of a therapeutic electromagnetic field. For example, treatment protocol generation method 200 may be re-executed when efficacy of treatment is to be evaluated.

Different embodiments are disclosed herein. Features of certain embodiments may be combined with features of other embodiments: thus certain embodiments may be combinations of features of multiple embodiments. The foregoing description of the embodiments of the invention has been presented for the purposes of illustration and description. It is not intended to be exhaustive or to limit the invention to the precise form disclosed. It should be appreciated by persons skilled in the art that many modifications, variations, substitutions, changes, and equivalents are possible in light of the above teaching. It is, therefore, to be understood that the appended claims are intended to cover all such modifications and changes as fall within the true spirit of the invention.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

The invention claimed is:

1. A protocol generation and treatment system comprising:
   a database storing a plurality of electrophysiological frequencies characteristic of known functionalities of human nervous systems;

a sensing assembly for receiving electrophysiological information from a patient having neurological disorders, impairment or limited functionality at at least some of said plurality of electrophysiological frequencies stored in said database, which are previously known to be associated with said neurological disorders, impairment or limited functionality;

an analyzer ascertaining at which ones of said plurality of electrophysiological frequencies, said electrophysiological information indicates said neurological disorders, impairment or limited functionality;

a personalized treatment generator operative using an output of said analyzer for generating a treatment for said patient including application of electromagnetic energy to said patient at at least some of those ones of said plurality of electrophysiological frequencies indicated to be associated with said neurological disorders, impairment or limited functionality; and at least one patient monitoring sensor for monitoring said patient during said treatment.

2. A protocol generation and treatment system according to claim 1 and wherein said personalized treatment generator is operative to modify at least one of a duration, a frequency and an amplitude of said electromagnetic energy in response to an output of said patient monitoring sensor.

3. A protocol generation and treatment system according to claim 1 and wherein said electromagnetic energy application subsystem is operative to apply said electromagnetic energy to at least most areas of a central nervous system of said patient.

4. A protocol generation and treatment system according to claim 1 and wherein said sensing assembly comprises an array of neural activity sensors.

5. A protocol generation and treatment system according to claim 4 and wherein said array of neural activity sensors comprises at least one of electroencephalography (EEG) and magnetoencephalography (MEG) sensors.

6. A protocol generation and treatment system according to claim 4 and wherein said array of neural activity sensors comprises at least one electro-physical sensor.

7. A protocol generation and treatment system according to claim 4 and wherein said array of neural activity sensors comprises at least one sensor for measuring neural activity in a part of the body of the patient other than the brain.

8. A protocol generation and treatment system according to claim 4 and wherein said array of neural activity sensors comprises an array of sensors along a spine of the patient.

9. A protocol generation and treatment system according to claim 1 and wherein said treatment protocol defines at least amplitude and duration of said electromagnetic energy to be applied to said patient at at least some of those ones of said plurality of electrophysiological frequencies indicated to be associated with said neurological disorders, impairment or limited functionality.

10. A protocol generation and treatment system according to claim 9 and wherein said treatment protocol also defines at least one of the following characteristics of said electromagnetic energy to be applied to said patient at at least some of those ones of said plurality of electrophysiological frequencies indicated to be associated with said neurological disorders, impairment or limited functionality:

order of application of electromagnetic energy at different ones of said plurality of electrophysiological frequencies;

intervals between successive applications of said electromagnetic energy; and periodicity of application of said electromagnetic energy.

11. A protocol generation and treatment system according to claim 9 and wherein said treatment protocol also defines at least two of the following characteristics of said electromagnetic energy to be applied to said patient at at least some of those ones of said plurality of electrophysiological frequencies indicated to be associated with said neurological disorders, impairment or limited functionality:

order of application of electromagnetic energy at different ones of said plurality of electrophysiological frequencies;

intervals between successive applications of said electromagnetic energy; and periodicity of application of said electromagnetic energy.

12. A protocol generation and treatment system according to claim 9 and wherein said treatment protocol also defines all of the following characteristics of said electromagnetic energy to be applied to said patient at at least some of those ones of said plurality of electrophysiological frequencies indicated to be associated with said neurological disorders, impairment or limited functionality:

order of application of electromagnetic energy at different ones of said plurality of electrophysiological frequencies;

intervals between successive applications of said electromagnetic energy; and periodicity of application of said electromagnetic energy.

13. A protocol generation and treatment system according to claim 4 and wherein said analyzer is operative to combine said electrophysiological information from a patient received from multiple ones of said array of said neural activity sensors.

* * * * *